United States Patent [19]

Heller

[11] 4,431,670
[45] Feb. 14, 1984

[54] D-PHENYLALANINE TREATMENT

[76] Inventor: Bernardo Heller, 921 N. 35 Ave., Hollywood, Fla. 33021

[21] Appl. No.: 363,974

[22] Filed: Feb. 4, 1982

Related U.S. Application Data

[62] Division of Ser. No. 218,285, Dec. 19, 1981, Pat. No. 4,355,044.

[51] Int. Cl.$^3$ ............................................. A61K 31/195
[52] U.S. Cl. ..................................................... 424/319
[58] Field of Search ........................................... 424/319

Primary Examiner—Stanley J. Friedman
Attorney, Agent, or Firm—Malin & Haley

[57] ABSTRACT

Method of treating pain, depression and Parkinsons disease using prescribed daily administration of D-phenylalanine alone, which has been found useful as an analgesic in warm blooded animals, as an antidepressant administered alone or in combination with another antidepressant, and useful for daily treatment of Parkinsons disease to reduce or eliminate particular symptoms and patient discomfort. Dosage may be orally, intramuscular or intravenous twice or more daily in 50–1000 mg amounts.

1 Claim, No Drawings

D-PHENYLALANINE TREATMENT

This application is a division of prior-filed, copending U.S. application Ser. No. 218,285 filed Dec. 19, 1981, now U.S. Pat. No. 4,355,044.

BACKGROUND OF THE INVENTION

Analgesics are substances that relieve or prevent pain without causing unconsciousness or completely deadening the nerve centers. Examples of conventional analgesic drugs are bromides, aspirin, morphine, opium, and belladonna. Morphine as an example has been used extensively as a pain killer in human treatment. One serious drawback to the use of morphine is that when used for extensive periods on a single patient, it is usually addictive. Other drawbacks are that morphine often produces serious side effects in many patients, including interference with heart and breathing, and vomiting. Aspirin, very effective for certain types of human pain, has limitations for most severe pain situations, and can result in undesirable side-effects.

The method of the present invention, employing prescribed dosages of D-phenylalanine, have demonstrated in controlled tests on human patients effectiveness as a pain killer equal to or superior to morphine, with no deleterious side effects and no patient addiction.

Treatment of manic depression, a major depressive disorder, up to the present has involved both psychological and biochemical means or combinations thereof, which have overall been unsuccessful. Drugs that have shown some promise in some patients have often caused severe traumatic side effects, resulting in other body damage to the patient.

Applicant has discovered that using D-phenylalanine independently in daily dosages, bipolar manic depression, depressive states, and unipolar depression can be successfully treated with no side effects to the patient. Recovery can be accomplished over a period of days and sustained by continuous daily administration with no short or long term deleterious side effects on the patient. Other antidepressant compositions may be used with D-phenylalanine without deleterious interaction.

Applicant has also discovered some relationship between the treatment of manic depression and Parkinsons disease. Parkinsons disease is a dehabilitary neurological disorder disturbing the motor function of the patient causing tremor, rigidity and other physiological symptoms. Specifically continuous daily administrations of D-phenylalanine alone extended over a period of days has been shown to dramatically improve the patients physiological and motor abilities, effectively alleviating the traumatic effect of the disease.

SUMMARY OF THE INVENTION

D-phenylalanine compositions are useful as an analgesic and are administered with such purpose in 50 mg–1000 mg two or more daily dosages to relieve or prevent pain in human beings and other warm blooded animals. The administration of D-Phenylalanine acts as a natural analgesic to be used in a short run for extreme pain or deep pain or can be used for long time periods such as for cancer patients as an effective treatment for the pain.

It is believed that the D-phenylalanine is transformed into phenethylamine in the central nervous system, allowing it to be effective as an analgesic.

D-phenylalanine has been found effective in the treatment of endogenous depression. In observing the recovery from certain cases of depression to the restoration of the patient to his normal working level, it was observed that depression is associated with the patient's phenethylamine daily urinary output. The results of tests show that D-phenylalanine has an improved theraputic effect on patients suffering with endogenous depression without collateral or toxic side effects. It is postulated that the metabolic pathway followed by the D-phenylalanine is such that the D-phenylalanine is directly decarboxylated to phenethylamine avoiding the catecholamine pathway entirely. It is also postulated that D-phenylalanine as an antidepressant raises the brain phenethylamine content, contrary to stimulate drugs like amphetamines which mimic the activity of phenethylamine in the central nervous system by acting on its receptors and also by liberating and depleting this substance in the brain after a certain time.

D-phenylalanine has also been found effective as a treatment for Parkinsons disease when administered daily to reduce the symptoms of the disease when the substance is taken on a daily basis over a period of time. Specifically D-phenylalanine has shown theraputic activities especially against rigidity, walking disability, speech difficulty, and psychic depression caused by the Parkinsons disease. The results were attained using D-phenylalanine alone in dosages ranging from 100 up to 1000 mgs daily distributed in two or more intakes such as morning and late afternoon daily. Patients were evaluated before and after neurologically during the treatment period for five parameters including rigidity, tremor, walking disability, speech difficulty and psychic depression. Improvements were found in all of the above parameters but with less results for tremor in the treatment of the Parkinsons disease.

It is an object of the invention to provide an effective analgesic for human beings and other warm-blooded animals that is non-addictive and causes no harmful side effects, even if administered over long periods of time.

It is another object of the invention to provide an effective treatment of unipolar and bipolar manic depression and depressive neurosis using biochemical techniques that produce no harmful patient side effects, and that allow the depression patients to return to a normal effective working attitude.

Yet another object of the invention is to provide a method for the continuous treatment of the symptomatic effects of Parkinsons disease for improving patients rigidity, walking abilities, improvement of speech difficulties and improvement in the area of psychic depression and tremor.

PREFERRED EMBODIMENT OF THE INVENTION

The following examples are presented to show the patient treatment using D-phenylalanine for the treatment of pain, depression, and Parkinsons disease.

EXAMPLE I

D-phenylalanine is administered for pain in all dosages between 50 mg–1000 mgs two or more times daily to relieve, reduce or prevent pain in human beings as an analgesic. Daily administration may be performed as required such as over long periods of time on a daily administrative basis for pain relief in cancer patients.

EXAMPLE II

D-phenylalanine is administered for the treatment of endogenous depression by administering D-phenylalanine in daily doses beginning with 100 mgs per day (50 mgs in the morning and 50 mgs at noon) for five days. The daily dosage may then be raised to 150 mgs for the next five days (100 mgs in the morning and 50 mgs at noon) and subsequently the dosage is raised to 200 mgs per day for five days. After this point based on the condition of the patient, which in observed testing, has shown in many instances complete euthymia the administration daily will be continued with a dosage level from between 50 mgs to 1000 mgs depending on the particular patient.

EXAMPLE III

The administration of D-phenylalanine for treatment of symptons of Parkinsons disease involves the administration of daily doses from between 200 and 500 mgs daily, distributed in two intakes, once in the morning and once in the late afternoon. Patients after one four week period under these dosages were evaluated for the treatment in five parameters including rigidity, tremor, walking disability, speech difficulties and psychic depression. The results obtained were significant with effect to rigidity, walking disabilities, speech difficulties, and psychic depression.

In reviewing the effects of D-phenylalanine in the treatment of pain, endogenous depression, and Parkinsons disease it is noted that preliminary studies indicate a dimunition of urinary phenethylamine elimination in Parkinsons disease patients and also diminished in endogenous depression. Phenethylamine is also present in the brain which is believed to antagonize pharmacologically induced Parkinson like states in animals. A proposed hypothesis about the neurohumoral mechanisms involved in extrapyramidal motility regulation supposes that Phenethylamine and Dopamine and Acetylcholine-Serotonine-Tryptamine control the activity of extrapyramidal structures whose balance can be disrupted by diminishing the activity of the Phenethylamine/Dopamine side or by increasing that of the Acetylcholine-Serotonine-Tryptamine side, both producing extrapyramidal disorders. The activity of the D-phenylalanine in contrast to its L-isomer may be explained by the fact that the D-phenylalanine will not follow the catecholamine pathway, not admitting the action of hydroxylase specific for the L-isomer form. In this way only the Phenethylamine concentration would be increased in the brain structures related to the extrapyramidal motility.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A method for the treatment of the symptoms of Parkinsons disease in human patients including the symptoms of rigidity, tremor, walking disabilities, speech difficulties and depression comprising the method of administering orally to said patients in two or more daily dosages, each between 50 mgs and 1000 mgs of D-phenylalanine on a daily basis to greatly reduce and improve rigidity, walking disabilities, speech difficulties and to relieve depression in a patient having Parkinsons disease.

* * * * *